United States Patent [19]

Bock et al.

[11] 4,309,540
[45] Jan. 5, 1982

[54] SUBSTITUTED PYRAZINYL-1,2,4-OXADIAZOLES

[75] Inventors: Mark G. Bock, Hatfield; Edward J. Cragoe, Jr.; Robert L. Smith, both of Lansdale, all of Pa.

[73] Assignee: Merck & Co., Inc., Rahway, N.J.

[21] Appl. No.: 151,494

[22] Filed: May 19, 1980

[51] Int. Cl.$^3$ .................... C07D 241/14; A61K 31/50
[52] U.S. Cl. ..................................... 544/405; 424/250
[58] Field of Search ........................................ 544/405

[56] References Cited

U.S. PATENT DOCUMENTS 3,313,813  4/1967  Cragoe, Jr.

OTHER PUBLICATIONS

Cragoe, et al., "J. Med. Chem.", vol. 10 (1967), pp. 66–75.
Watthey, et al., "J. Med. Chem.", vol. 23, (1980), 690–692.
Cecil et al., "A Textbook of Medicine", (1957), p. 1251.
Adams, et al, "J. Org. Chem.", vol. 18 (1953), p. 934.
Eloy, "Fortschr. Chem. Forsch", vol. 4 (1965), p. 807.
Clapp, "Adv. Het. Chem", vol. 20 (1976), p. 65.
Warburton, "J. Chem. Soc.", (1966), p. 1522.
Strani et al., "Gazz. Chim. Ital.", vol. 93, (1963), 482.

*Primary Examiner*—Anton H. Sutto
*Attorney, Agent, or Firm*—Raymond M. Speer; Michael C. Sudol, Jr.

[57] ABSTRACT

Novel substituted pyrazinyl-1,2,4-oxadiazoles and processes for preparing the same. The compounds are useful in the treatment of edema and hypertension.

8 Claims, No Drawings

SUBSTITUTED PYRAZINYL-1,2,4-OXADIAZOLES

SUMMARY OF THE INVENTION

The novel compounds of this invention are depicted in Formula I and the corresponding quaternary salts are represented by Formula II.

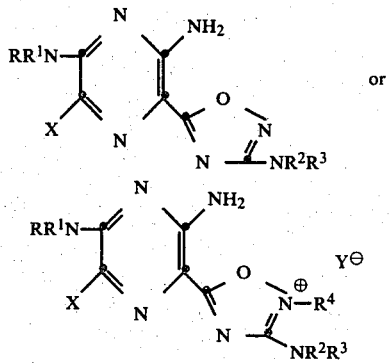

wherein
R is hydrogen or lower alkyl ($C_{1-5}$) such as methyl, ethyl, isopropyl, n-butyl, n-pentyl;
$R^1$ is hydrogen or lower alkyl ($C_{1-5}$) such as methyl, ethyl, isopropyl, n-butyl, n-pentyl;
$R^2$ is hydrogen or lower alkyl ($C_{1-5}$) such as methyl, ethyl, isopropyl, n-butyl, n-pentyl;
$R^3$ is hydrogen or lower alkyl ($C_{1-5}$) such as methyl, ethyl, isopropyl, n-butyl, n-pentyl;
R and $R^1$ can be joined to form an alkylene group of from 2–4 carbon atoms such as an ethylene or butylene chain;
$R^4$ is lower alkyl ($C_{1-5}$) such as methyl, ethyl, isopropyl, n-butyl or n-pentyl;
X is halo such as fluoro, chloro, bromo or iodo, cyano or phenyl; and
Y is halide as chloride, bromide or iodide or another suitable anion such as methanesulfonate or p-toluenesulfonate.

The preferred compounds of this invention are those compounds of Formulae I and II wherein
R is hydrogen or methyl;
$R^1$ is hydrogen or methyl;
$R^2$ is hydrogen or methyl;
$R^3$ is hydrogen or methyl;
$R^4$ is methyl;
X is halo; and
Y is chloride, bromide or iodide.

Specifically preferred compounds of this invention are
3-Amino-5-[3-amino-5-dimethylamino-6-chloropyrazin-2-yl]-1,2,4-oxadiazole.
2-Methyl-3-amino-5-[3-amino-5-dimethylamino-6-chloropyrazin-2-yl]-1,2,4-oxadiazolium iodide.
3-Amino-5-[3,5-diamino-6-chloropyrazin-2-yl]-1,2,4-oxadiazole.
2-Methyl-3-amino-5-[3,5-diamino-6-chloropyrazin-2-yl]-1,2,4-oxadiazolium iodide.
3-Dimethylamino-5-[3,5-diamino-6-chloropyrazin-2-yl]-1,2,4-oxadiazole.
2-Methyl-3-dimethylamino-5-[3,5-diamino-6-chloropyrazin-2-yl]-1,2,4-oxadiazolium iodide.

The compounds of this invention as shown by Formulae I and II and the preferred compounds discussed above are useful because they possess diuretic, naturetic and antikaluretic properties and can be used in the treatment of conditions associated with electrolyte imbalance such as in the treatment of edema and associated hypertension. Furthermore, the compounds of this invention differ markedly in their solubility properties. Thus, while those compounds of Formula I are soluble in non-polar organic solvents such as toluene, ether and the like, their counterparts of Formula II dissolve readily in polar mileux such as water, dimethylsulfoxide, and the like.

The products of this invention can be administered to patients (both human and animal) in the form of pills, tablets, capsules, elixirs, injectable preparations and the like. They can be administered either orally or parentally or any other feasible method as known to those skilled in the art such as intravenously or in the form of suppositories and the like.

The type of formulation to be administered can be comprised of one or more of the compounds of this invention as the only essential active ingredient of the pharmaceutical formulation. The formulations are merely combinations of the active ingredient mentioned with pharmaceutically inert carriers and the like. Several pharmaceutical formulations are prepared as shown in Examples 4 and 5.

The compounds of this invention are advantageously administered at a dosage range of from about 5 mg. to about one gram per day or a somewhat higher or lower dosage at the physician's discretion, preferably in subdivided amounts on a 2 to 4 times a day regimen and most preferably at a dosage range from 10 to 500 mg. per day. It will be realized by those skilled in the art that the dosage range for any particular patient (animal or human) will depend upon the severity of the disease treated, weight of the patient and any other condition which the physician or other person skilled in the art will take account of.

The compounds of this invention can be administered as shown above either alone with the general pharmaceutical carriers or in combination with other kaluretic diuretics such as, for example in combination with hydrochlorothiazide and the like with pharmaceutical carriers.

Example 6 shows the preparation of a typical combination product. The combination dosage in a typical formulation to be administered as described above is 5–100 mg. of a compound of this invention with 50–100 mg. of a kaluretic diuretic such as hydrochlorothiazide. Generally a good ratio between the two active ingredients is 1 to 10 (compound of this invention to the kaluretic diuretic). The combination products can be administered in similar dosages as that described above for the administration of a single compound of this invention. Again, it will be realized that the dosage range for any particular patient will depend on the severity of the disease being treated, weight of the patient and any other conditions which the physician or other person skilled in the art will take account of.

The compounds disclosed in this invention in Formulae I and II and the preferred compounds can be formed according to one or more of the processes described below.

Method A

This method is used for the preparation of compounds of Formula I. It can be depicted by the following equation:

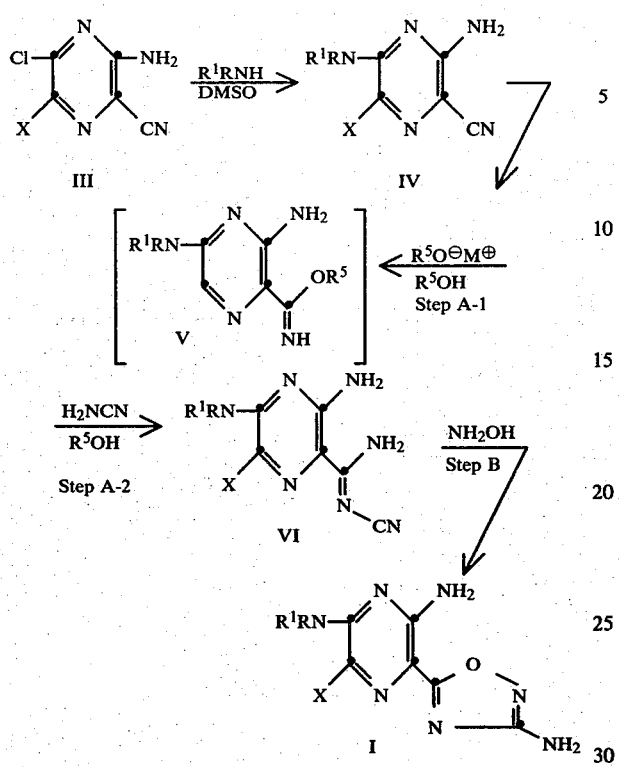
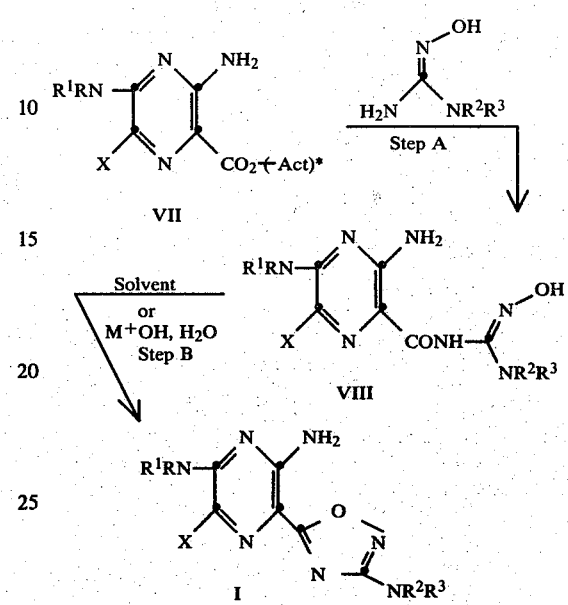

Another method for the preparation of compounds of Formula I can be shown by the following equation further referred to as Method B.

Method B

In the above equation the radicals R, R¹ and X are as defined previously for Formula I. $R^5$ is a straight or branched-chain lower alkyl group with up to 10 carbon atoms and $M^+$ is an alkalai metal cation such as lithium, sodium, potassium and the like.

The Method A synthesis involves the reaction of a 2-cyanopyrazine IV, generated from III as indicated in Method A, with an alkalai metal alkoxide, $R^5O^-M^+$, e.g., sodium methoxide, in a suitable alcohol, $R^5OH$, e.g., methanol, to give the desired intermediate imino ether V. Other alcohols, $R^5OH$, especially lower aliphatic alcohols and their corresponding lithium, sodium or potassium alkoxides, may be used to form the desired imino ether V. The reaction is carried out in the chosen solvent for 1 to 36 hours at room temperature or by heating on a steam bath for a lesser time. The intermediate imino ether V is not isolated as such but rather the reaction mixture is rendered neutral by the addition of an equivalent amount (or a stoichiometric amount) of a suitable acid (like HCl, acetic acid, sulfuric acid, etc.) and treated directly with cyanamide in the same solvent. In this way, the cyanoamidine VI is formed within 1 to 24 hours.

In Step B of this method A, the cyanoamidine of formula VI is treated in a suitable solvent such as tetrahydrofuran with an equivalent amount of hydroxylamine to provide the product which is usually recovered from the reaction mixture by extraction or precipitation with water. The reaction can be carried out either in a protic (e.g., methanol, ethanol, etc.) or an aprotic (e.g., tetrahydrofuran, dioxane, dimethoxyethane) solvent or, preferably, in a combination of solvents at temperatures ranging from room temperature to the boiling point of the solvent(s) for 1 to 36 hours. The crude reaction product may be purified by recrystallization from a suitable solvent (e.g., methanol, ethyl acetate and the like) or by chromatography.

In the above equation, the radicals R, R¹, R², R³ X and $M^+$ are as defined previously for Formula I and in Method A. The radical (Act)* is either $R^5$ (as previously defined) or $-C(CH_3)=CHCONHC(CH_3)_3$, $-CON(C_6H_5)_2$ or the like.

Method B involves two steps of which the first is reaction of an activated pyrazine ester VII with a 1,1-disubstituted hydroxyguanidine to give the N-pyrazinoyl derivative VIII. The starting hydroxyguanidine is added to a stirred suspension of the desired pyrazine ester VII in a suitable solvent like isopropanol, dimethylformamide and the like and the whole is heated at reflux from 0.5 to 1 hour or stirred at room temperature until consumption of the pyrazine ester VII is complete as evidenced by thin layer chromatography. The desired intermediate VIII can be isolated by precipitation with water and purified by recrystallization. Alternatively, the intermediate VIII can be taken without isolation directly to the final product by simply extending the time of reaction in Step A. The title compound I is thus produced by a thermal cyclization-dehydration reaction. Other solvents like N-methylpyrrolidone or N-methylmorpholine may also be used.

In another variation, the 1,2,4-oxadiazide ring of I is formed by treating an aqueous suspension of the N-pyrazinoyl derivative VIII with a suitable base, $M^+O^-H$, such as sodium hydroxide and the like, at room temperature in water. Other bases such as lithium or potassium hydroxide, alkali metal carbonates and alkali metal bicarbonates may be substituted for sodium hydroxide. Further, the reaction may be carried out in alcohols such as methanol, ethanol, isopropanol, etc. using the corresponding alkali metal alkoxide as a base. In addition, aprotic solvents like dioxane, tetrahydrofuran, dimethylformamide etc. may also be used to effect this cyclization. In this instance, amines such as triethyl amine, ethyl diisopropylamine, 1,5-diazabicyclo[4.3.0]-non-5-ene, 1,5-diazabicyclo[5.4.0]undec-5-ene, morpholine, pyridine, etc. can be used as the preferred base. The reaction is then best carried out at temperatures ranging from 0° to 120° but preferably at room temperature for 0.5 to 10 hours. The title compound I is isolated either by filtration or by extraction with a polar solvent like methylene chloride or ethylacetate and then is purified by recrystallization.

The compounds of Formula II can be prepared by the following process known as Method C. An equation for this method is shown below.

Method C

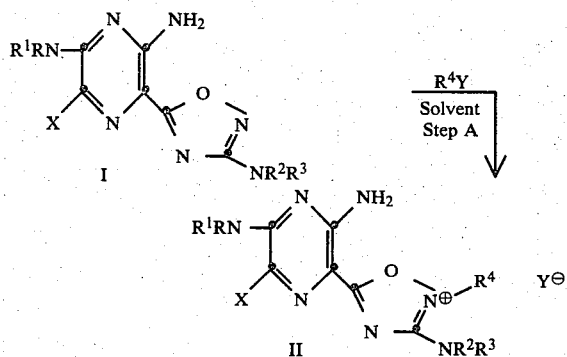

In the above process the radicals, R, $R^1$, $R^2$, $R^3$, $R^4$, X and $Y^-$ are as defined previously for Formulae I and II.

In method C, the 3-substituted-5-(pyrazin-2-yl)-1,2,4-oxadiazole I is dissolved in a suitable solvent like N-methylpyrrolidinone but preferably N,N-dimethylformamide and treated with a lower alkyl halide $R^4X$, preferably methyl iodide. The resulting solution is allowed to stand at room temperature for 2 to 5 days or at temperatures not exceeding 45° C. for up to 24 hours. The solid product II is collected by filtration and is purified by recrystallization.

The following examples describe the preparation of certain compounds which are illustrative of the novel compounds of this invention, and certain specific dosage forms suitable for administering the novel compounds. It is to be understood that the invention is not to be limited to the specific compounds described in the examples or by the specific reaction condition described for the preparation of these compounds or by the specific ingredients included in the pharmaceutical preparations, but is to be understood to embrace variations and modifications thereof which fall within the scope of the appended claims.

EXAMPLE 1

Preparation of
3-Amino-5-(3-amino-5-dimethylamino-6-chloropyrazin-2-yl)-1,2,4-oxadiazole Step A: Preparation of
N-cyano-3-amino-5-dimethylamino-6-chloropyrazine-2-carboxamidine 3-Amino-5-dimethylamino-6-chloropyrazinylnitrile (46.1 g, 0.233 mole) is added in one portion to a solution of methanol (800 ml) containing sodium methoxide (2.48 g., 0.046 mole). The resulting reaction mixture is stirred at room temperature for 30 hours, then filtered to remove traces of insoluble material and the filtrate is treated with 2.63 ml (0.046 mole) of acetic acid to make the reaction mixture neutral. The filtrate is concentrated to a total volume of approximately 200 ml. This solution of the imino ether is then treated in one portion with cyanamide (10.51 g, 0.25 mole) and the resulting clear reaction mixture is allowed to stand at room temperature. Within 1.5 hours a yellow solid precipitates. The solid is collected by filtration after 5 hours have elapsed to give 19.5 g of the desired product. Further concentration of the filtrate affords an additional 2.6 g of the product. Recrystallization of the crude product from methanol affords an analytical sample of the title compound as a bright yellow solid, m.p. 223°–224° C.

Elemental analysis for $C_8H_{10}N_7Cl$: Calc.: C, 40.08; H, 4.21; N, 40.91. Found: C, 40.60; H, 4.22; N, 41.10.

IR(KBr, partial): 3400, 3150, 2190, 1600, 1550, 810, 775 cm$^{-1}$.

$^{13}$Cnmr (DMSO-d$_6$): 40.54, 111.31, 115.76, 119.63, 152.61, 153.48, 165.11 ppm.

Step B: Preparation of
3-Amino-5-(3-amino-5-dimethylamino-6-chloropyrazin-2-yl)-1,2,4-oxadiazole To a solution of tetrahydrofuran (250 ml) containing 50 ml of methanol and 12.36 g (51.57 mmole) of N-cyano-3-amino-5-dimethylamino-6-chloropyrazinecarboxamidine is added hydroxylamine hydrochloride (6.65 g, 103.13 mmole) and triethylamine (21.56 ml, 154.71 mmole). The resulting reaction mixture is protected from moisture (calcium chloride) and heated to reflux for 6 hours. The reaction mixture is cooled, poured into water (1 l) and the yellow solid which forms is collected by filtration. Concentration of the filtrate affords more solid which when combined with the first crop yields 12.64 g (96%) of the desired product. The reaction product is dried at 60° C. and directly affords analytically pure 3-amino-5-(3-amino-5-dimethylamino-6-chloropyrazin-2-yl)-1,2,4-oxadiazole, m.p. 210°–211° C.

Elemental analysis for $C_8H_{10}N_7OCl$: Calc. C, 37.58; H, 3.94; N, 38.35; Cl, 13.86. Found: C, 37.49; H, 3.84; N, 38.20; Cl, 13.79.

IR(KBr, partial): 1635, 1580, 1540, 1390, 1180, 910, 780 cm$^{-1}$.

$^{13}$Cnmr (DMSO-d$_6$): 40.6, 108.5, 120.7, 151.4, 153.3, 167.8, 170, 1 ppm.

EXAMPLE 2

Preparation of
3-Amino-5-(3,5-diamino-6-chloropyrazin-2-yl)-1,2,4-oxadiazole

Step A: Preparation of
3,5-diamino-6-chloro-N-(hydroxyiminoaminomethylene)pyrazine-2-carboxamide See U.S. Pat. No. 3,577,418, Column 18, lines 5–21.

Step B: Preparation of
3-Amino-5-(3,5-diamino-6-chloropyrazin-2-yl)-1,2,4-oxadiazole A suspension of 3,5-diamino-6-chloro-N-(hydroxyiminoaminomethylene)pyrazine-2-carboxamide (23.82 g, 0.97 mole) in 200 ml of isopropanol containing 2.3 g. (0.1 mole) of sodium is refluxed on a steam bath for 12 hours. The reaction mixture is cooled and filtered to give the title compound as a dark yellow solid. The analytical sample is prepared by dissolving the crude product in warm dimethylformamide and adding water until the solution becomes almost turbid. The crystals obtained in this way are collected and dried in vacuo over phosphorus pentoxide to give the title compound in pure form as a bright yellow solid, m.p. 278° C., (dec.).

Elemental analysis for $C_6H_6N_7O$ Cl: Calc.: C, 31.66; H, 2.66; N, 43.08. Found: C, 31.97; H, 2.71; N, 43.27.

IR(KBr, partial): 3460, 3140, 1600, 1400, 1250, 1050, 880, 760 cm$^{-1}$.

Dmr (DMSO-d$_6$): 6.2 (2H, broad S,); 7.35 (4H, broad s)δ.

$^{13}$Cnmr (DMSO-d$_6$): 107.27; 120.13; 152.73; 153.22; 167.70, 170.35 ppm.

EXAMPLE 3

Preparation of 2-Methyl-3-amino-5-(3-amino-5-dimethylamino-6-chloropyrazin-2-yl)-1,2,4-oxadiazolium iodide To 2 ml of dry dimethylformamide is added 340 mg (1.33 mmole) of 3-amino-5-(3-amino-5-dimethylamino-6-chloropyrazin-2-yl)-1,2,4-oxadiazole. The resulting yellow solution is treated with 4 ml (64.3 mmole) of iodomethane. The homogeneous reaction mixture is protected from moisture (CaCl$_2$) and allowed to stand at 40° C. overnight. The reaction mixture is cooled to room temperature and filtered to collect the solid which precipitated during the course of the reaction. The solid is washed with ether and air dried to afford 470 mg. (88T) of the title compound in pure form; m.p. 300°. The title compound can be further purified, if desired, by recrystallization from ethanol to give fine, yellow needles.

ir(KBr, partial): 3075, 1670, 1520, 1465, 1395, 1180, 950 cm$^{-1}$.

UV$_{max}$(EtOH): 392 nm.

Pmr (DMSO-d$_6$): 3.28 (6H, S, N(CH$_3$)$_2$), 3.88 (3H, S, N⊕-CH$_3$), 7.53 (2H, NH$_2$pyrazine ring), 9.3 (2H, NH$_2$, oxadiazole ring)δ.

$^{13}$Cnmr (DMSO-d$_6$): 36.43, 41.01, 103.51, 122.67, 153.56, 153.71, 161.59, 168.69 ppm.

EXAMPLE 4

Compressed Tablet containing 50 mg. of active ingredient.

| | Per tablet, Mg. |
|---|---|
| 3-Amino-5-(3,5-diamino-6-chloro-pyrazin-2-yl)-1,2,4-oxadiazole | 50 |
| Calcium phosphate dibasic | 200 |
| Ethyl cellulose (as 5% solution in ethanol) | 5 |
| Unmixed granulation | 255 |
| Add: | |
| Starch, corn | 14 |
| Magnesium stearate | 1 |
| | 270 |

Directions: Mix the active ingredient above and calcium phosphate and reduce to a No. 60 mesh powder. Granulate with Ethocel in alcohol and pass the wet granulation through a No. 10 screen. Dry the granulation at 110° F. for 12-18 hours. Dry grind to a No. 20 mesh. Incorporate the "adds" and compress into tablets each weighing 270 mg.

EXAMPLE 5

Dry filled capsule containing 50 mg. of active ingredient.

| | Per capsule, mg. |
|---|---|
| 3-Amino-5-(3,5-diamino-6-chloro-pyrazin-2-yl)-1,2,4-oxadiazole | 50 |
| Lactose | 273 |
| Magnesium stearate | 2 |
| Mixed powders | 325 |

Mix the active ingredient above, lactose, and magnesium stearate and reduce to a No. 60 mesh powder. Encapsulate, filling 325 mg. in each No. 2 capsule.

The above formulations can be employed to prepare compressed tablets or capsules of other novel compounds of this invention hereinbefore described.

EXAMPLE 6

Combination dosage form in dry filled capsule.

| | Per capsule, mg. |
|---|---|
| 3-Amino-5-(3,5-diamino-6-chloro-pyrazin-2-yl)-1,2,4-oxadiazole | 10 |
| Hydrochlorothiazide | 50 |
| Magnesium stearate | 2 |
| Lactose | 73.5 |
| Mixed powders total | 185.51 |

Mix all of the above ingredients, reduce to a No. 60 mesh powder and encapsulate filling 105.5 mg. in each No. 2 capsule.

What is claimed is:

1. A compound of the formula:

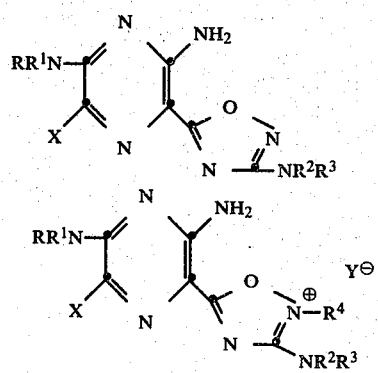

wherein
R is hydrogen or lower alkyl (C$_{1-5}$),
R$^1$ is hydrogen or lower alkyl (C$_{1-5}$),
R$^2$ is hydrogen or lower alkyl (C$_{1-5}$),
R$^3$ is hydrogen or lower alkyl (C$_{1-5}$),
R and R$^1$ can be joined to form with an alkylene group of from 2-4 carbon atoms,
R$^4$ is lower alkyl (C$_{1-5}$)
X is halo, cyano or phenyl, and
Y$^-$ is chloride, bromide or iodide, or a suitable anion.

2. A compound of Formulae I and II:

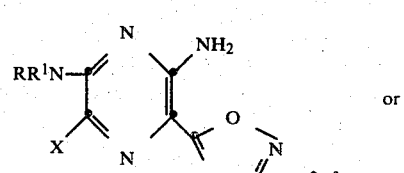

-continued

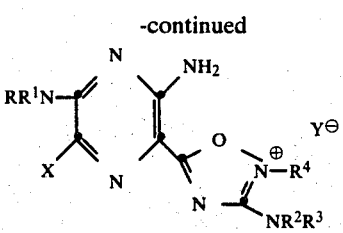

wherein
R is hydrogen or methyl;
R¹ is hydrogen or methyl;
R² is hydrogen or methyl;
R³ is hydrogen or methyl;
R⁴ is methyl;
X is halo; and
Y⁻ is chloride, bromide or iodide.

3. A compound of claim 2 wherein R=R¹=methyl; R²=R³=hydrogen; and X=chloro which is 3-amino-5-[3-amino-5-dimethylamino-6-chloropyrazin-2-yl]-1,2,4-oxadiazole.

4. A compound of claim 2 wherein R=R¹=R⁴=methyl; R²=R³=hydrogen; X is chloro and Y⁻ is iodide which is 2-methyl-3-amino-5-[3-amino-5-dimethylamino-6-chloropyrazin-2-yl]-1,2,4-oxadiazolium iodide.

5. A compound of claim 2 wherein R=R¹=R²=R³=hydrogen and X is chloro which is 3-amino-5-[3,5-diamino-6-chloropyrazin-2-yl]-1,2,4-oxadiazole.

6. A compound of claim 2 wherein R=R¹=R²=R³=hydrogen; R⁴ is methyl; X is chloro and Y⁻ is iodide which is 2-methyl-3-amino-5-[3,5-diamino-6-chloropyrazin-2-yl]-1,2,4-oxadiazolium iodide.

7. A compound of claim 2 wherein R=R¹=hydrogen; R²=R³=methyl and X is chloro which is 3-dimethylamino-5-[3,5-diamino-6-chloropyrazin-2-yl]-1,2,4-oxadiazole.

8. A compound of claim 2 wherein R=R¹=hydrogen; R²=R³=R⁴=methyl; X is chloro and Y⁻ is iodide which is 2-methyl-3-dimethylamino-5-[3,5-diamino-6-chloropyrazin-2-yl]-1,2,4-oxadiazolium iodide.

* * * * *